United States Patent
Fukushima et al.

(10) Patent No.: US 8,564,767 B2
(45) Date of Patent: Oct. 22, 2013

(54) DEFECT INSPECTING APPARATUS AND DEFECT INSPECTING METHOD

(75) Inventors: Hideki Fukushima, Hitachinaka (JP); Nobuaki Hirose, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/821,468

(22) PCT Filed: Jul. 26, 2011

(86) PCT No.: PCT/JP2011/066958
§ 371 (c)(1),
(2), (4) Date: Apr. 23, 2013

(87) PCT Pub. No.: WO2012/043039
PCT Pub. Date: Apr. 5, 2012

(65) Prior Publication Data
US 2013/0208270 A1      Aug. 15, 2013

(30) Foreign Application Priority Data
Sep. 27, 2010 (JP) .................................. 2010-215383

(51) Int. Cl.
*G01N 21/00* (2006.01)
(52) U.S. Cl.
USPC .................... 356/237.5; 356/237.1; 356/237.3
(58) Field of Classification Search
USPC ....................................................... 356/237.5
See application file for complete search history.

(56) References Cited

U.S. PATENT DOCUMENTS

| | | | | |
|---|---|---|---|---|
| 4,054,361 A | * | 10/1977 | Noguchi | .................... 359/218.1 |
| 4,886,959 A | | 12/1989 | Hoshi et al. | |
| 5,251,010 A | * | 10/1993 | Maltby, Jr. | .................... 356/613 |
| 5,473,426 A | * | 12/1995 | Hayano et al. | ............. 356/237.2 |
| 5,748,305 A | * | 5/1998 | Shimono et al. | ........... 356/237.2 |
| 6,411,377 B1 | * | 6/2002 | Noguchi et al. | ........... 356/237.4 |

(Continued)

FOREIGN PATENT DOCUMENTS

| | | |
|---|---|---|
| JP | 62-089336 A | 4/1987 |
| JP | 63-136333 A | 6/1988 |

(Continued)

OTHER PUBLICATIONS

International Preliminary Report on Patentability received in International Application No. PCT/JP2011/066958 dated Apr. 25, 2013.

*Primary Examiner* — Gregory J Toatley
*Assistant Examiner* — Jarreas C Underwood
(74) *Attorney, Agent, or Firm* — Mattingly & Malur, PC

(57) ABSTRACT

The defect inspecting apparatus is capable of easily performing adjustment with a change of an elevation angle of illumination to a substrate to be inspected, while being low in cost. A plane parallel plate and a cylindrical lens supported by a lens holder are symmetrically disposed at the same tilt angle θ with respect to a horizontal plane. A shift in optical axis at a focal position of light (101) with the rotation of the cylindrical lens can be prevented from occurring. The light can be rotated with a motor and a belt by a rotating mechanism, while allowing the optical axes of the light to match each other at the same focal position. The lens holder and the rotating mechanism are connected to a vertically moving mechanism and moved along a guide of the vertically moving mechanism to thereby adjust the focal position of the cylindrical lens.

10 Claims, 4 Drawing Sheets

(56) References Cited

U.S. PATENT DOCUMENTS

| | | | |
|---|---|---|---|
| 6,608,676 B1 * | 8/2003 | Zhao et al. | 356/237.2 |
| 7,164,475 B2 * | 1/2007 | Fairley et al. | 356/237.2 |
| 7,333,192 B2 * | 2/2008 | Nakano et al. | 356/237.2 |
| 8,107,065 B2 * | 1/2012 | Nakano et al. | 356/237.3 |
| 8,218,138 B2 * | 7/2012 | Nakano et al. | 356/237.2 |
| 2006/0203231 A1 | 9/2006 | Uto et al. | |
| 2007/0177136 A1 | 8/2007 | Nakano et al. | |
| 2008/0144024 A1 | 6/2008 | Nakano et al. | |
| 2009/0079973 A1 | 3/2009 | Uto et al. | |
| 2009/0122303 A1 | 5/2009 | Nakano et al. | |
| 2010/0265496 A1 | 10/2010 | Nakano et al. | |
| 2011/0063603 A1 | 3/2011 | Nakano et al. | |

FOREIGN PATENT DOCUMENTS

| | | |
|---|---|---|
| JP | 08-271437 A | 10/1996 |
| JP | 2000-105203 A | 4/2000 |
| JP | 2001-056300 A | 2/2001 |
| JP | 3566589 B2 | 6/2004 |
| JP | 2006-250739 A | 9/2006 |
| JP | 2007-192759 A | 8/2007 |
| WO | 2009/139155 A1 | 11/2009 |

* cited by examiner

DEFECT INSPECTING APPARATUS AND DEFECT INSPECTING METHOD

TECHNICAL FIELD

The present invention relates to a defect inspecting apparatus and a defect inspecting method that inspect defects that will be present on a semiconductor, a liquid crystal display device, etc.

BACKGROUND ART

In a semiconductor manufacturing process, foreign matters and pattern defects become a cause of failure such as defective electrical insulation and short circuits between wires if they exist on a semiconductor substrate (wafer). If miniaturization of semiconductor devices proceeds and fine foreign matters are present accordingly, even finer foreign matters will become causes of defective electrical insulation of its capacitor and destruction of a gate oxide film and the like.

These foreign matters include those that come from moving parts in a semiconductor conveying device, those produced from human bodies, those produced through reaction in a processing device by process gases, those with chemicals and materials mixed therein, etc., all of which are mixed therein in various states.

Likewise, even in a manufacturing process of a liquid crystal display device, it becomes unusable as a display device if foreign matters adhere onto a pattern or some defect takes place therein. This means that the situation is the same even in a printed circuit board manufacturing process. Adherence of foreign matters becomes a cause of short circuits and defective electrical connections in the pattern.

In a prior art, as one technology for detecting finer foreign matters and defects on a semiconductor substrate at high speed and with high sensitivity, there has heretofore been disclosed as described in Patent Document 1, defect inspecting apparatus which irradiates a laser on the semiconductor substrate and thereby detects light scattering from foreign matters produced where the foreign matters adhere onto the semiconductor substrate, and which compares the result of its detection with the result of immediately preceding inspection of a semiconductor substrate of the same type to thereby eliminate false information that might be caused by a pattern, thus providing high sensitivity and high reliability.

A method of avoiding the entrance of a 0th-order diffracted light from a pattern into the entrance pupil of a detection lens by means of laser irradiating means which enables highly sensitive and reliable inspection of foreign matters and defects has been described in Patent Document 2.

Namely, Patent Document 2 has described that a relationship between the elevation angle of illuminating light, its azimuthal angle and the numerical aperture of the detection lens is set so as to satisfy a predetermined condition to thereby avoid the entrance of the zeroth-order diffracted light.

In Patent Document 2 as well, an illuminating lens having a conical curved surface has been used to narrow down an XY plane of illumination incident obliquely with respect to a substrate to be inspected in a Y direction and produce a slit-shaped beam spot collimated in an X direction. The illuminating lens has a section of a flat convex lens whose focal distance changes linearly along its longitudinal direction.

PRIOR ART LITERATURE

Patent Document

Patent Document 1: JP-62-89336-A
Patent Document 2: Japanese Patent No. 3566589

SUMMARY OF THE INVENTION

Problems to be Solved by the Invention

In the above-described defect inspecting apparatus, detectable defects of interest can be expanded if the elevation angle of illumination is made variable and various objects are irradiated with illuminating light.

In the related art, however, when the elevation angle of illumination was changed as the technology described in Patent Document 2, the setting and adjustment of preventing the zeroth-order diffracted light from entering were cumbersome and therefore the adjustment mechanism was also complicated.

Further, although the illuminating lens for producing the collimated slit-shaped beam spot has made use of the cylindrical lens having the conical curved surface as described in Patent Document 2, the cylindrical lens is a lens which is hard in processing, low in production yield and expensive, thus resulting in an increase in the cost of the defect inspecting apparatus.

An object of the present invention is to realize a defect inspecting apparatus and a defect inspecting method capable of easily performing adjustment with a change of an elevation angle of illumination to a substrate to be inspected, while being low in cost.

Means for Solving the Problems

In order to achieve the above object, the present invention is conFigured as follows.

A defect inspecting apparatus of the present invention includes a laser light source and a beam spot shaping section. The beam spot shaping section includes a beam shaping part which has a plane parallel plate for allowing a laser from the laser light source to penetrate therethrough and a cylindrical lens for shaping the laser having penetrated the plane parallel plate, and a beam alignment part which reflects the beam having penetrated the beam shaping part and irradiate the beam on an object to be inspected, as a linear beam spot and which is capable of changing an elevation angle of the reflected beam relative to the object. The defect inspecting apparatus further includes a detection optical system which detects scattering light reflected from the object; and a control system which detects a defect present on the object, based on the scattering light detected by the detection optical system.

A defect inspecting method of the present invention includes the steps of allowing a laser from a laser light source to penetrate a plane parallel plate and thereafter allowing the laser to penetrate a cylindrical lens for shaping the laser to thereby form a linear beam; reflecting the linear beam and irradiating the linear beam on the object as a linear beam spot; and detecting scattering light reflected from the object and detecting a present on the object, based on the detected scattering light.

Effects of the Invention

The present invention can realize a defect inspecting apparatus and a defect inspecting method capable of easily performing adjustment with a change of an elevation angle of illumination to a substrate to be inspected, while being low in cost.

MODE FOR CARRYING OUT THE INVENTION

An embodiment of the present invention will be described hereinafter with reference to the accompanying drawings. Incidentally, in the following drawings, similar functional portions are denoted by the same reference signs.

Embodiment 1

An apparatus conFiguration of an inspecting apparatus according to an embodiment 1 of the present invention will be described with reference to FIGS. 1 through 8. Incidentally, the embodiment shown below is an example in which the present invention is applied to a defect inspecting apparatus for a semiconductor wafer. The present invention is however applicable to a defect inspecting apparatus for a liquid crystal display device and the like and a defect inspecting method therefor as well as to the defect inspecting apparatus for the semiconductor wafer.

Figure 1:
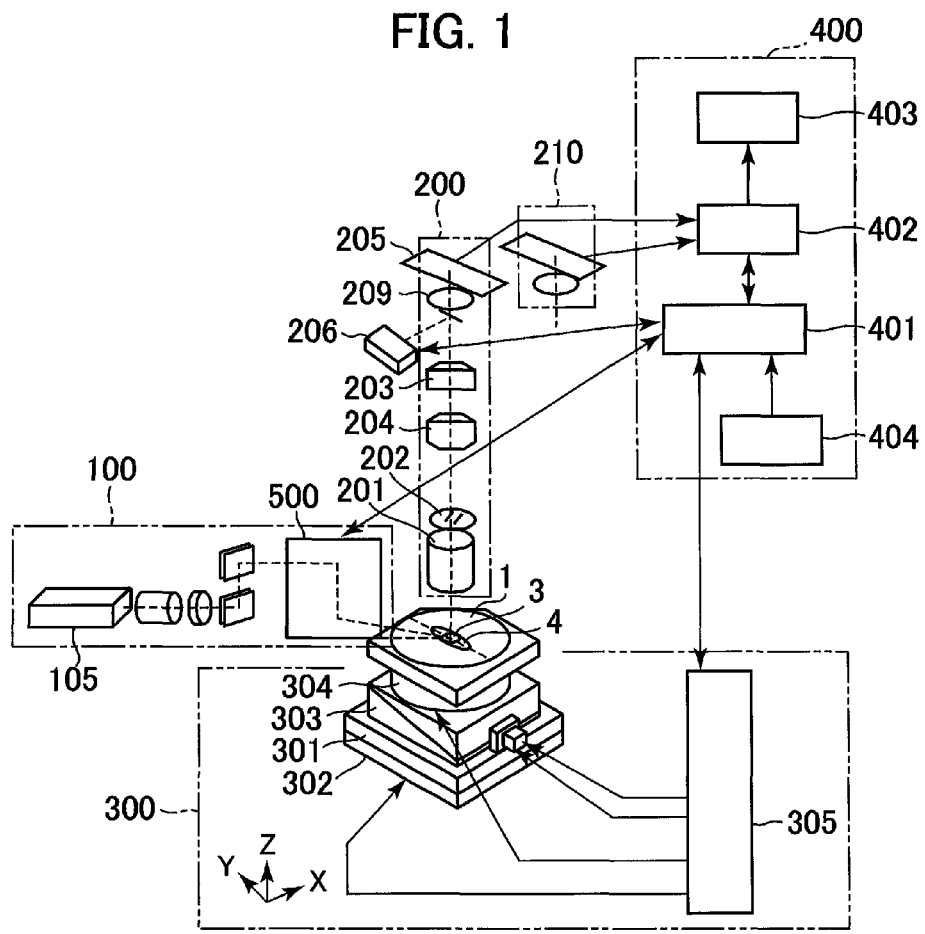
FIG. 1 is an overall schematic conFiguration diagram of a defect detecting apparatus to which the present invention is applied.

Referring to FIG. 1, the defect inspecting apparatus includes a stage part 300 with a substrate 1 to be inspected mounted thereon. The stage part 300 has an X stage 301 and a Y stage 302 which scan a beam spot 3 being a slit-shaped illumination area irradiated on the substrate 1 in slit form, a detection area 4 in an image sensor, and an inspection area in the substrate 1 respectively in XY directions and which are movable relative to an optical system; a Z stage 303 capable of focusing on the surface of the substrate 1; a theta θ stage 304; and a stage controller 305.

The defect inspecting apparatus includes an illumination optical system 100 having a laser light source 105, a beam expander, an optical branching element (or mirror) being switchable among an optical filer group, a mirror and a glass plate, and a beam spot shaping section 500.

Incidentally, the details of the beam spot shaping section 500 will be described later.

Further, the defect inspecting apparatus includes a detection optical system 200, and a branched-detection optical system 210 for performing simultaneous inspections using two sensors. The detection optical system 200 has a detection lens 201, a spatial filter 202, an image forming lens 203, a zoom lens group 204, a one-dimensional image sensor 205, an upper observation system 206 enabling the detection area in the image sensor 205 to be observed, and a polarized-beam splitter 209.

Further, the defect inspecting apparatus includes a control system 400. The control system 400 has a control CPU part 401, a signal processor 402, a display part 403 and an input part 404. The signal processor 402 includes an A/D converter, a data memory capable of delaying a signal, a differential processing circuit which determines a difference between signals in each chip, a memory which temporarily stores the difference between the signals in each chip, a threshold value calculating processor which sets a pattern threshold value, and a comparator. The control CPU part 401 recognizes and stores a beam position and corrects and controls the beam position. The control CPU part 401 controls driving of the motors, the coordinates and the sensor. The control CPU part 401 also includes a storage part which stores control data therein.

The defect inspecting apparatus includes an output part which stores a result of detection of defects such as foreign matters and outputs the result of detection thereof.

A third harmonic generator (THG) of a high-power YAG laser with a wavelength of 355 nm may preferably be used as the laser light source of the illumination optical system 100. The wavelength does not however have to be 355 nm. That is, an Ar laser, a nitrogen laser, a He—Cd laser, an excimer laser or the like, and another light source may be used as the laser light source.

The one-dimensional image sensor 205 may be a CCD sensor or a TDI (Time Delay Integration) sensor. The CCD sensor may be considered to be suitable for linear detection because each pixel size is about 10 µm. The sensitivity of the CCD sensor is not reduced when an image out of focus in a scanning direction is captured.

In the TDI sensor, on the other hand, it is desirable that an amount of the captured image out of focus should be reduced by measures such as narrowing an illumination width or tilting the TDI sensor, etc., because the TDI sensor integrates an image corresponding to a predetermined number of pixels in the scanning direction.

An XYZ coordinate system is shown in the lower left in the stage part 300 of FIG. 1. An XY axis is taken on the plane of the stage part 300, and a Z axis is taken vertically upward. The optical axis of the detection optical system 200 is disposed along the Z axis.

The detailed conFiguration and operation of the beam spot shaping section 500 will next be explained in detail using FIGS. 2 through 8.

Figure 2:
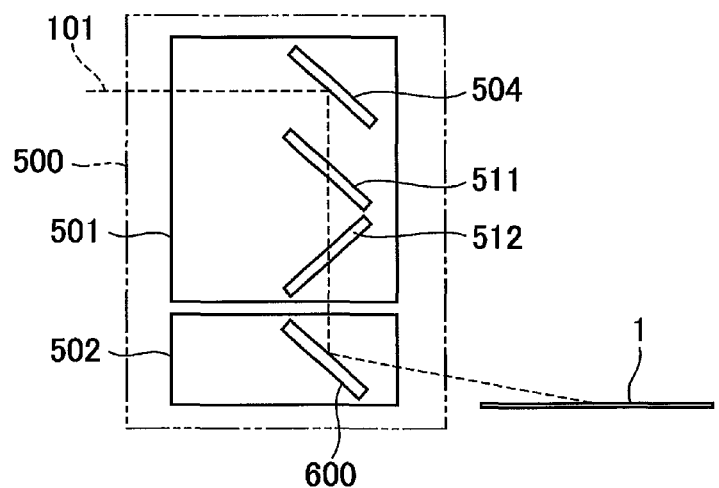
FIG. 2 is a schematic conFiguration diagram of a beam spot shaping section of a defect inspecting apparatus according to an embodiment 1 of the present invention.

FIG. 2 is a schematic conFiguration diagram of the beam spot shaping section 500.

In FIG. 2, the beam spot shaping section 500 includes a beam shaping part 501 and a beam alignment part 502.

Figure 3:
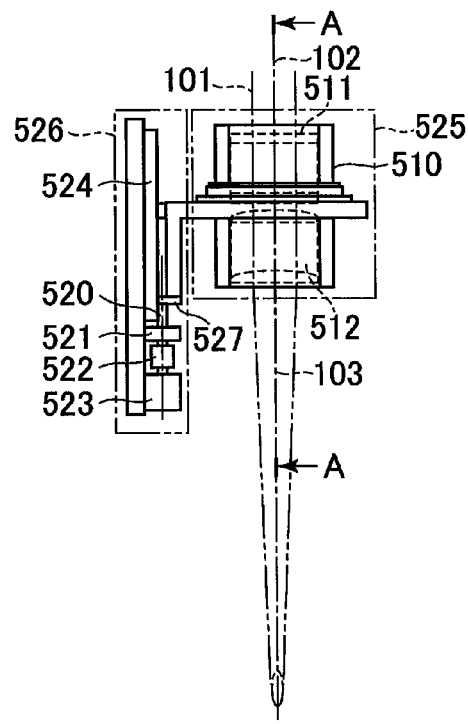
FIG. 3 is a side view of a beam shaping part of the defect inspecting apparatus according to the embodiment 1 of the present invention.
Figure 4:
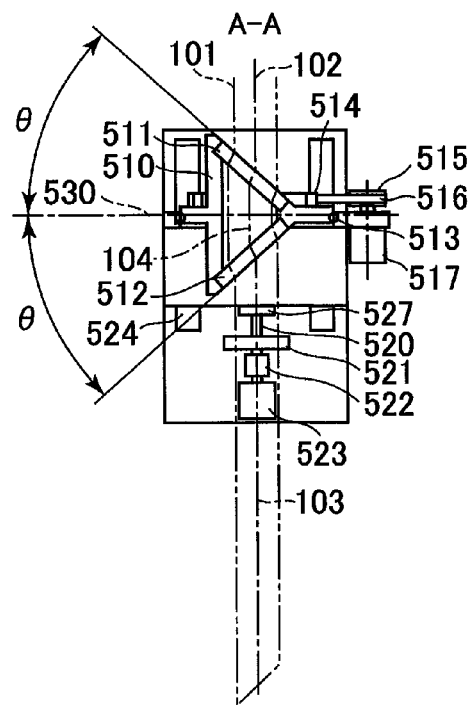
FIG. 4 is a sectional view taken along line A-A of the beam shaping part shown in FIG. 3.
Figure 5:
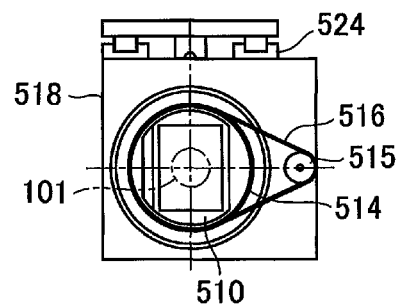
FIG. 5 is a schematic plan view of the beam shaping part of the defect inspecting apparatus according to the embodiment 1 of the present invention.
Figure 6:
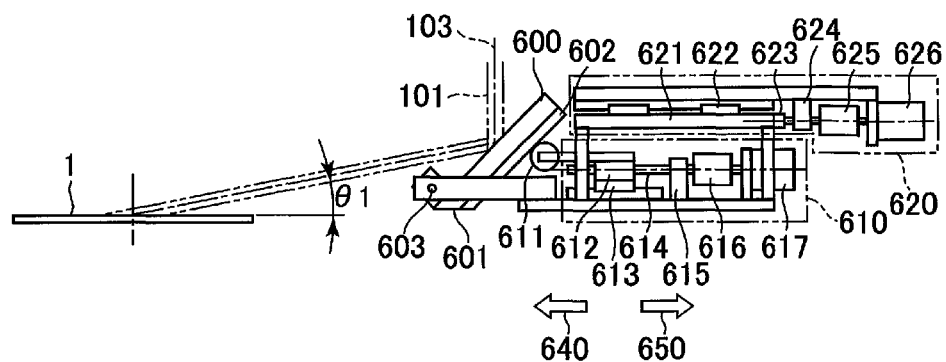
FIG. 6 is a side view of a beam alignment part of the defect inspecting apparatus according to the embodiment 1 of the present invention.
Figure 7:
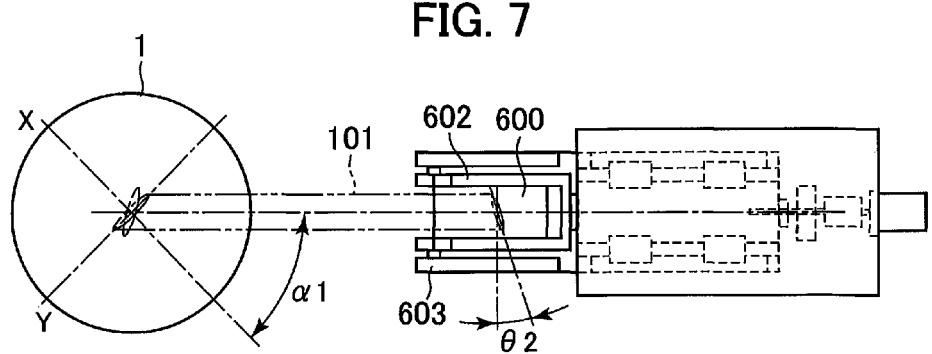
FIG. 7 is a schematic plan view of the beam alignment part of the defect inspecting apparatus according to the embodiment 1 of the present invention.
Figure 8:
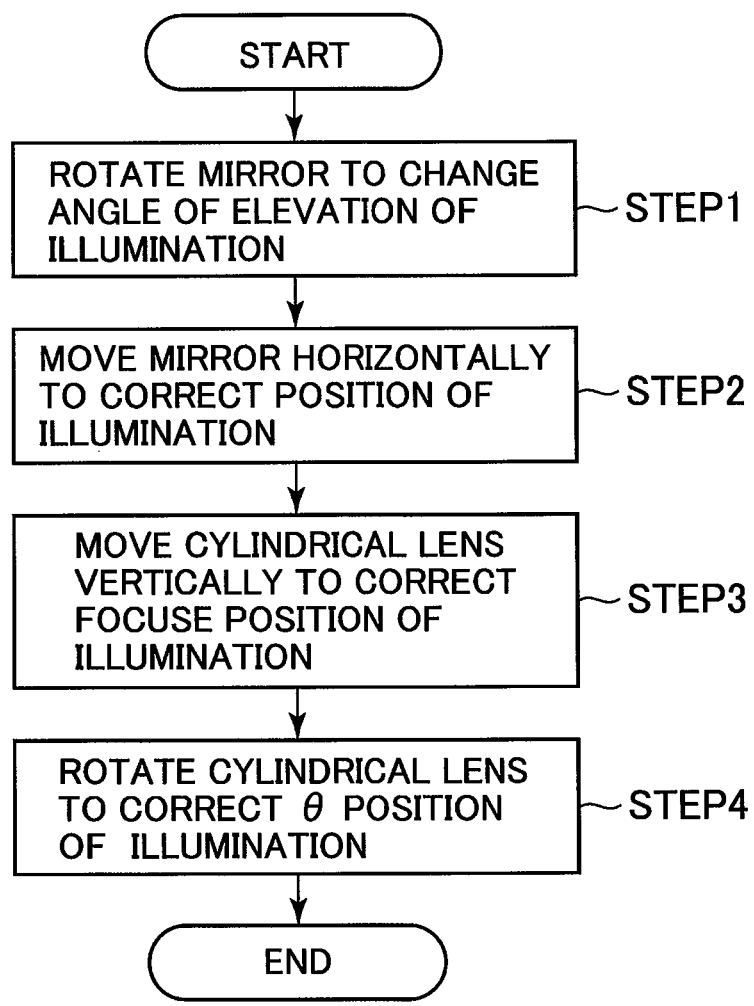
FIG. 8 is a flowchart for the operation of switching of an elevation angle of illumination in the embodiment 1 of the present invention.

FIG. 3 is a side view of the beam shaping part 501, FIG. 4 is a sectional view taken along line A-A of the beam shaping part 501 shown in FIG. 3, and FIG. 5 is a plan view of the beam shaping part 501. FIG. 6 is a side view of the beam alignment part 502, and FIG. 7 is a plan view of the beam alignment part 502. FIG. 8 is a flowchart for the operation of switching of the elevation angle of the beam spot shaping section 500.

In FIG. 2, light 101 emitted from the light source 105 is reflected by a mirror 504 and enters a plane parallel plate 511 (e.g., blank glass). The light 101 having passed (penetrated) through the plane parallel plate 511 is gathered on a cylindrical lens 512 and shaped into a linear beam. Thereafter, the linear beam is reflected by a mirror 600 and irradiated on the subject 1 to be inspected.

In FIGS. 3, 4 and 5, the plane parallel plate 511 and the cylindrical lens 512 are built in a lens holder 510. Here, the lens holder 510 supports the plane parallel plate 511 and the cylindrical lens 512 from both side faces in such a manner as not to block the light 101. A portion of the lens holder 510, through which at least light 101 passes, has been exposed.

The plane parallel plate 511 and the cylindrical lens 511 are disposed at the same tilt angle θ with respect to a horizontal plane 530 lying between these and in such a manner as to be symmetric with each other with the horizontal plane interposed therebetween. That is, the plane parallel plate 511 is arranged inclined by the same angle as the azimuthal angle of the linear beam applied to the object 1 to be inspected, with respect to the plane 530 perpendicular to the optical axis 102 of the laser emitted from the laser light source 105. The cylindrical lens 512 is arranged in a position where it is symmetric with respect to the plane parallel plate 511 with the plane normal to the optical axis 102 of the laser being placed therebetween. Further, the thickness of the plane parallel plate 511 is approximately the same as that of the cylindrical lens 512.

With the arrangement of the plane parallel substrate 511, the optical axis 104 of the light 101 moved parallel by the plane parallel plate 511 is caused to move parallel by the cylindrical lens 511, thereby enabling the incoming optical axis 102 and the outgoing optical axis 103 to be aligned on the same axis.

The plane parallel substrate 511 is placed in front of the cylindrical lens 512 to make it possible to prevent a shift in the optical axis of the light 101 at a focal position thereof with the rotation of the cylindrical lens 512 and to enable the light 101 to be rotated while the optical axes of the light 101 remain coincident with each other at the same focal position.

Further, the lens holder 510 is connected to the rotating mechanism 525 as shown in FIG. 3. The rotating mechanism 525 will be explained in detail.

The rotating mechanism 525 includes a pulley 514 connected to the lens holder 510, a bearing 513 of the lens holder 510, a drive-side pulley 515, a timing belt 516 that connects the pulley 514 and the drive-side pulley 515, a motor 517 connected to the drive-side pulley 515, and a support table 518.

The support table 518 of the rotating mechanism 525 has an aperture that mounts the lens holder 510 therein. The lens holder 510 is rotated in a state in which the light 101 has penetrated the plane parallel plate 511 and the cylindrical lens 512 in the lens holder 510 mounted in the aperture to thereby enable the light 101 to be rotated about the incoming optical axis 102 of the light 101.

Providing the rotating mechanism 525 in this manner enables the light 101 to be rotated in the state in which the focal position of the light 101 is being held in the same position. Further, the lens holder 510 and the rotating mechanism 525 are connected to a vertically moving mechanism 526 to adjust the focal position of the cylindrical lens 512. That is, the plane parallel plate 511 and the cylindrical lens 512 are moved along the direction of the optical axis 102 of the laser emitted from the laser light source 105 by means of the vertically moving mechanism 526. Incidentally, the lens holder 510 and the vertically moving mechanism 526 may be connected to the rotating mechanism 525.

The vertically moving mechanism 526 will next be described in detail.

The vertically moving mechanism 526 includes a connecting portion 527 (e.g., a nut of a ball screw) that connects the rotating mechanism 525 and the ball screw 520, a ball screw fixing part 521, a motor 523, a coupling 522 that couples the ball screw 520 and the motor 523, and a guide 524 which guides the cylindrical lens 512 in a focusing direction.

The lens holder 510 and the rotating mechanism 525 are moved along the guide 524 of the vertically moving mechanism 526 to thereby make it possible to adjust the focal position of the cylindrical lens 512.

Further, the position of rotation of the light 101 at the same focal position of the cylindrical lens 512, and the focal position of the cylindrical lens 512 can be adjusted independent of each other.

Descriptions will next be provided for the mirror 600 using FIG. 6.

The mirror 600 is arranged inclined relative to the plane parallel to the substrate 1 to be inspected. Further, the end face 601 of the mirror 600 on the substrate 1 side becomes a surface which is tilted relative to its plane portion and which is parallel to the plane parallel to the substrate 1 or close parallel thereto. That is, the mirror 600 is formed in a state tilted relative to the substrate 1 in such a manner that the end face 601 of the mirror 600 on the substrate 1 side becomes approximately parallel to the substrate 1.

With this shape of the mirror 600, the mirror 600 can be brought close to the substrate 1 in its tilted state, so that low elevation angle illumination can be formed.

Further, the mirror 600 is arranged inclined at a tip portion of a linearly moving mechanism 610 through a mirror holder 602 for supporting the mirror 600. Here, the neighborhood of the end face 601 is supported by a rotating shaft 603, and the mirror 600 is disposed rotatably through the mirror holder 602. Thus, when the linearly moving mechanism 610 is moved, the mirror 600 is conFigured so as to rotate about the rotating shaft 603.

The linearly moving mechanism 610 will next be described.

The linearly moving mechanism 610 includes a connecting portion 612 that connects a bearing 611 and a ball screw 614, a ball screw fixing part 615, a coupling 616 that connects the ball screw 614 and a motor 617, and a guide 613 that guides the bearing 611 in the direction indicated by each of arrows 640 and 650.

Here, the bearing 611 is rotatably arranged between the linearly moving mechanism 610 and the mirror 600. With the arrangement of the bearing 611, the bearing 611 presses the mirror holder 602 while the bearing 611 is rotating with the movement of the linearly moving mechanism 610, thereby moving the mirror 600 rotationally. Consequently, friction with the rotating operation of the mirror 600 can be reduced, thereby making it possible to suppress dust emissions.

Further, some of the mirror holder 602, specifically, a portion thereof brought into contact with the bearing 611 has been given hardening. The portion subjected to the hardening is higher in hardness than other portions. Increasing the hardness in this way enables suppression of dust emissions.

Further, preferably, it is desirable that the hardness of the portion of the mirror holder 602, which has been given hardening, and the hardness of the bearing 611 are at the same level as each other so as to make it possible to prevent the dust emissions to the utmost.

Thus, the illuminating light can be adjusted to an arbitrary angle of elevation by rotating the mirror 600 by means of the linearly moving mechanism 610.

Further, the linearly moving mechanism 610 and the mirror 600 are connected to a linearly moving mechanism 620.

The linearly moving mechanism 620 will next be explained.

The linearly moving mechanism 620 includes a connecting portion 621 that connects the linearly moving mechanism 610 and the ball screw 623, a ball screw fixing part 624, a coupling 625 that connects the ball screw 623 and a motor 626, and a guide 622 that guides the linearly moving mechanism 610 in the direction indicated by each of the arrows 640 and 650.

The linearly moving mechanism 610 and the mirror 600 are moved integrally by the linearly moving mechanism 620 to enable a change in the irradiation position of the illuminating light 101 due to a change of the elevation angle of the illuminating light 101 to be adjusted.

When, for example, the mirror 600 is rotated in the direction in which an elevation angle θ1 of the illuminating light 101 relative to the substrate 1 becomes large, the linearly moving mechanism 610 is moved in the direction indicated by the arrow 640.

A relationship between linear illumination and an azimuthal angle formed on the substrate 1 by use of the cylindrical lens 512 will next be described.

FIG. 7 is a plan view of the beam alignment part 502 shown in FIG. 6 and is a plan view taken where the substrate 1 is seen from above.

First, the azimuthal angle means the azimuth of illumination relative to the X-axis direction (scanning direction) in the stage part 300 (angle α1 in FIG. 7).

In the one embodiment of the present invention, the linear illumination is irradiated from the azimuthal angle α1 (e.g., 45°) to prevent a 0th-order diffracted light from the substrate 1 from being detected by a detector of the detection optical system 200.

Here, in the defect inspecting apparatus according to the one embodiment of the present invention, the detector is disposed parallel to a Y axis shown in FIG. 7. If the linear illuminating light (linear beam) is not parallel to the Y axis, then an uninspectable area is formed because the detector is not capable of receiving all scattering light from the linear illuminating light. Thus, the linear illumination also needs to be parallel to the Y axis.

When, however, the cylindrical lens 512 is parallel to the substrate 1 in a state in which the linear illumination has the azimuthal angle α1, a variable elevation angle is taken in the one embodiment of the present invention. Therefore, when the optical path of the light 101 is bent by means of the mirror 600, the focal plane of the linear illumination is tilted relative to the Y axis.

Thus, in the one embodiment of the present invention, the cylindrical lens 512 is tilted relative to the plane parallel to the wafer corresponding to the substrate 1. More specifically, the cylindrical lens 512 is tilted by the same angle as the azimuthal angle α1. That is, α1=θ. Here, θ is the angle shown in FIG. 4.

Further, in order to prevent a shift in the optical axis between the incoming optical axis 102 and the outgoing optical axis 103, the plane parallel plate 511 is tilted by the same angle θ in the direction opposite to the direction in which the cylindrical lens 512 is tilted. That is, the plane parallel plate 511 is set to a state shown in FIG. 4.

Here, it is desirable that the plane parallel plate 511 is identical to the cylindrical lens 512 in material and thickness. This is because if they are identical in material and thickness, the refractive index of the plane parallel plate 511 and the refractive index of the cylindrical lens 512 become equal to each other in a simple conFiguration, so that the incoming optical axis 102 and the outgoing optical axis 103 can be made identical with each other without changing the optical characteristics of the light 101.

Incidentally, the plane parallel plate 511 may be different from the cylindrical lens 512 in material and thickness. For example, when the refractive index of the plane parallel plate 511 is higher than the refractive index of the cylindrical lens 512, the tilted angle of the plane parallel plate 511 may be set smaller than that of the cylindrical lens 512.

When the plane parallel plate 511 is thicker than the cylindrical lens 512 in thickness, the tilted angle of the plane parallel plate 511 may be set smaller than that of the cylindrical lens 512.

A method of changing an elevation angle while the azimuthal angle α1 is kept as it is will next be explained with reference to a flowchart of FIG. 8. Specifically, descriptions will be provided for a method of increasing the elevation angle while the azimuthal angle α1 is kept as it is. Here, the elevation angle means the angle of incidence of the linear illumination in the direction perpendicular to the plane of the substrate 1 (angle θ1 in FIG. 6).

First, at STEP1 of FIG. 8, the linearly moving mechanism 610 is moved in the direction (direction indicated by the arrow 640) close to the substrate 1 to rotate the mirror 600. Thus, the tilted angle of the mirror 600 increases so that the angle of elevation of the linear illumination also becomes large. When the elevation angle is set larger here, the illuminated position of the linear illumination changes relative to the horizontal direction of the plane of the substrate 1, and the focal plane thereof also changes relative to the vertical direction of the plane of the substrate 1. Further, the linear illumination rotates on the plane of the substrate 1.

Thus, at STEP2, to adjust a change in the horizontal direction, i.e., to irradiate the same horizontal position as before the change of the elevation angle with the linear illumination, the linearly moving mechanism 620 is moved to move the mirror 600 in the horizontal direction. More specifically, the linearly moving mechanism 620 is moved in the direction to approach the substrate 1 to thereby move the mirror 600 in the direction to approach the substrate 1. Consequently, the linear illumination is applied onto the same horizontal position as before the change of the elevation angle.

When the illumination elevation angle θ1 is changed while the linear illumination remains kept parallel to the Y axis, the light 101 rotates at the reflective surface of the mirror 600. It is therefore necessary to allow the angle of rotation of the light 101 and the angle of rotation of the cylindrical lens 512 to coincide with each other.

The following relational expression (1) is established between the illumination elevation angle θ1 and a tilt θ2 of the light 101 at the surface of the mirror 600:

$$\theta 2 = \arctan(\sin \theta 1) \quad (1)$$

Next, at STEP3, in order to adjust a change in the focal plane of the illuminating light 101 in the vertical direction, i.e., to cause the focal plane to match with the surface of the substrate 1, the vertically moving mechanism 526 is moved in an upward direction (direction away from the substrate 1). It is thus possible to match the focal plane with the surface of the substrate 1.

Further, at STEP4, to adjust the rotation of the linear illumination, the rotating mechanism 525 is rotated corresponding to the change in elevation angle. Consequently, the rotation of the linear illumination can be adjusted.

The angle of rotation of the mirror 600 (the position of movement of the linearly moving mechanism 610), the position of horizontal movement of the mirror 600 (the position of movement of the linearly moving mechanism 620), the vertical position of the cylindrical lens 512 (the vertical position of the vertically moving mechanism 526), the position of rotation of the cylindrical lens 512 (the position of rotation of the rotating mechanism 525) all taken where a plurality of illumination elevation angles are set with respect to a predetermined azimuthal angle, have been stored in the storage part of the control CPU part 401 in the defect inspecting apparatus.

If an arbitrary illumination elevation angle is designated and input from the input part 404, the control CPU part 401 reads the rotation angle of the mirror 600 or the like corresponding to the input illumination elevation angle from the storage part and controls the linearly moving mechanism 610 or the like, based on the read data.

According to the one embodiment of the present invention as described above, the cylindrical lens 512 is tilted by the same angle as the azimuthal angle to make the linear illumination parallel to the Y axis. Further, the plane parallel plate 511 is arranged in the position where it is symmetric with respect to the cylindrical lens 512 with the horizontal plane placed therebetween to allow the incident light to enter the cylindrical lens 512 through the plane parallel plate 511 and to bring the incoming optical axis and the outgoing optical axis to the same axis.

Thus, while being low-cost in conFiguration, the linear illuminating light can take on the form parallel to the Y axis regardless of variations in azimuthal angle, and a shift in the optical axis at the focal position with the rotation of the cylindrical lens 512 can be prevented from occurring.

The plane parallel plate 511 and the cylindrical lens 512 are configured so as to be movable in the vertical direction and in such a manner that their rotational movement and horizontal movement are made possible.

Therefore, an adjustment in the position of the linear illuminating light, an adjustment in its focus and an adjustment in its rotation with a change of an elevation angle of the linear illuminating light irradiated on a substrate to be inspected can be easily performed.

DESCRIPTION OF REFERENCE NUMERALS

1 . . . Substrate to be inspected (wafer), 3 . . . Beam spot (illumination area), 4 . . . Detection area of image sensor, 100 . . . Illumination optical system, 101 . . . Incident light, 102 . . . Incoming optical axis, 103 . . . Outgoing optical axis, 105 . . . Light source, 200 . . . Detection optical system, 201 . . . Detection lens (objective lens), 202 . . . Spatial filter, 203 . . . Image forming lens, 204 . . . Zoom lens group, 205 . . . Image sensor, 206 . . . Observation optical system, 209 . . . Polarized-beam splitter, 210 . . . Branched detection optical system, 300 . . . Stage part, 301 . . . Y stage, 302 . . . X stage, 303 . . . Z stage, 304 . . . θ stage, 305 . . . Stage controller, 400 . . . Control system, 401 . . . Control CPU part, 402 . . . Signal processor, 403 . . . Display part, 404 . . . Input part, 500 . . . Beam spot shaping section, 501 . . . Beam shaping part, 502 . . . Beam alignment part, 510 . . . Lens holder, 511 . . . Plane parallel plate, 512 . . . Cylindrical lens, 525 . . . Rotating mechanism, 526 . . . Vertically moving mechanism, 600 . . . Mirror, 602 . . . Mirror holder, 610, 620 . . . Linearly moving mechanisms.

The invention claimed is:

1. A defect inspecting apparatus which inspects a defect present on an object to be inspected, comprising:
a laser light source which generates a laser;
a beam spot shaping section including a beam shaping part which has a plane parallel plate for allowing the laser from the laser light source to penetrate therethrough, and a cylindrical lens for shaping the laser having penetrated the plane parallel plate to thereby form a linear beam, and a beam alignment part which reflects the beam having penetrated the beam shaping part and irradiates the beam on the object as a linear beam spot, the beam alignment part being capable of changing an elevation angle of the reflected beam relative to the object;
a stage part which supports the object;
a detection optical system which detects scattering light reflected from the object supported by the stage part;
a control system which controls operations of the beam spot shaping part, the stage part and the detection optical system and detects a defect present on the object, based on the scattering light detected by the detection optical system;
wherein the plane parallel plate is arranged inclined by the same angle as an azimuthal angle of the linear beam irradiated on the object, with respect to a plane perpendicular to an optical axis of the laser from the laser light source, and
wherein the cylindrical lens arranged in a position thereof symmetric with the plane parallel plate with the plane interposed therebetween.

2. The defect inspecting apparatus according to claim 1, wherein the beam shaping part includes:
a vertically moving mechanism which moves the plane parallel plate and the cylindrical lens along the optical axis of the laser from the laser light source; and
a rotating mechanism which rotates the plane parallel plate and the cylindrical lens with the optical axis of the laser as a central axis, and the control system operates the vertically moving mechanism according to the elevation angle of the beam relative to the object to adjust a focal position of the beam spot and operates the rotating mechanism to adjust a position of rotation of the linear beam spot on the object.

3. The defect inspecting apparatus according to claim 2, wherein the beam alignment part includes:
a mirror part which is rotatably supported about a rotating shaft and reflects the beam having penetrated the beam shaping part;
a rotational moving mechanism which rotationally moves the mirror part; and
a linearly moving mechanism which moves the mirror part and the rotational moving mechanism in a linear direction, and the control system operates the rotational moving mechanism to adjust the elevation angle of the beam relative to the object and operates the linearly moving mechanism to adjust a position of illumination of the beam spot.

4. The defect inspecting apparatus according to claim 3, wherein the rotational moving mechanism presses the mirror part in a linear direction to rotatably move the mirror part about the rotating shaft.

5. The defect inspecting apparatus according to claim 4, wherein the control system has a data storage part which stores a position of the rotational moving mechanism that presses the mirror part, a vertical position of the vertically moving mechanism, a position of rotation of the rotating mechanism, and a position of the linearly moving mechanism therein for every plural elevation angle of the beam relative to the object, and the control system controls the operation of the beam spot shaping part in accordance with the data stored in the data storage part.

6. A defect inspecting method of inspecting a defect present on an object to be inspected, comprising the steps of:
generating a laser from a laser light source;
allowing the laser to penetrate a plane parallel plate and thereafter allowing the laser to penetrate a cylindrical lens for shaping the laser to thereby form a linear beam;
reflecting the linear beam penetrated through the cylindrical lens and irradiating the linear beam on the object as a linear beam spot;
detecting scattering light reflected from the object and detecting a defect present on the object, based on the detected scattering light;
arranging the plane parallel plate inclined by the same angle as an azimuthal angle of the linear beam irradiated on the object, with respect to a plane perpendicular to an optical axis of the laser from the laser light source; and
arranging the cylindrical lens in a position thereof symmetric with the plane parallel plate with the plane interposed therebetween.

7. The defect inspecting method according to claim 6, including the steps of:
moving the plane parallel plate and the cylindrical lens along the direction of the optical axis of the laser according to the elevation angle of the beam relative to the object to adjust a focal position of the beam spot, and
rotating the plane parallel plate and the cylindrical lens with the optical axis of the laser as a central axis to adjust a position of rotation of the linear beam spot on the object.

8. The defect inspecting method according to claim 7, including the steps of:
reflecting the linear beam penetrated through the cylindrical lens by a mirror part rotatably supported about a rotating shaft,
rotationally moving the mirror part to thereby adjust the elevation angle of the beam relative to the object, and
moving and operating the mirror part in a linear direction to adjust a position of illumination of the beam spot.

9. The defect inspecting method according to claim 8, wherein the mirror part is pressed in the linear direction to rotationally move about the rotating shaft.

10. The defect inspecting method according to claim 9, including the steps of:
storing a position of rotational movement of the mirror part, vertical positions of the plane parallel plate and the cylindrical lens along the direction of the optical axis of the laser from the laser light source, and positions of rotation of the plane parallel plate and the cylindrical lens in a data storage part for every plural elevation angle of the beam relative to the object, and
adjusting the position of the rotational movement of the mirror part, the vertical positions of the plane parallel plate and the cylindrical lens, and the rotational positions thereof in accordance with the data stored in the data storage part.

\* \* \* \* \*